United States Patent
Stergiou

(10) Patent No.: US 9,675,258 B2
(45) Date of Patent: Jun. 13, 2017

(54) STREAMING UPDATES OF CENTRAL MOMENTS FOR HEART RATE VARIABILITY QUANTIFICATION

(71) Applicant: FUJITSU LIMITED, Kawasaki-shi, Kanagawa (JP)

(72) Inventor: Stergios Stergiou, East Palo Alto, CA (US)

(73) Assignee: FUJITSU LIMITED, Kawasaki (JP)

( * ) Notice: Subject to any disclaimer, the term of this patent is extended or adjusted under 35 U.S.C. 154(b) by 313 days.

(21) Appl. No.: 14/261,187

(22) Filed: Apr. 24, 2014

(65) Prior Publication Data

US 2015/0305634 A1    Oct. 29, 2015

(51) Int. Cl.
*A61B 5/024* (2006.01)
*A61B 5/0245* (2006.01)

(52) U.S. Cl.
CPC ........ *A61B 5/02405* (2013.01); *A61B 5/0245* (2013.01)

(58) Field of Classification Search
CPC ..................... A61B 5/02405; A61B 5/0245
See application file for complete search history.

(56) References Cited

U.S. PATENT DOCUMENTS

| | | | |
|---|---|---|---|
| 9,301,695 B2* | 4/2016 | Stergiou | A61B 5/0205 |
| 2008/0208016 A1* | 8/2008 | Hughes | A61B 5/0533 |
| | | | 600/301 |

OTHER PUBLICATIONS

N. Dagres et al., "Influence of the duration of Holter monitoring on the detection of arrhythmia recurrences after catheter ablation of atrial fibrillation: Implications for patient follow-up" International Journal of Cardiology, vol. 139, Issue 3, Mar. 18, 2010, pp. 305-306.
Moving average, http://en.wikipedia.org/wiki/Moving_average, retrieved Apr. 24, 204.

* cited by examiner

*Primary Examiner* — Mark W Bockelman
(74) *Attorney, Agent, or Firm* — Maschoff Brennan

(57) ABSTRACT

A computer readable storage medium configured to cause a system to perform operations of computing the standard deviation of a plurality of K−1 most recent heart beat intervals and a current heart beat interval (I1) from a plurality of consecutive heart beat intervals, from a sum (S1) of K most recent heart beat intervals squared and the sum (S2) of the K most recent heart beat intervals and a Kth oldest heart beat interval (I2). The computer readable storage medium calculates an updated sum (S1') of S1 minus I2 squared plus I1 squared and the updated sum (S2') of S2 minus I2 plus I1, and a square root of the sum of the ratio of S1' to K and of the ratio of the square of S2' to the square of K.

11 Claims, 9 Drawing Sheets

STREAMING UPDATES OF CENTRAL MOMENTS FOR HEART RATE VARIABILITY QUANTIFICATION

FIELD

The present invention relates to a system and method for performing streaming updates of central moments for heart rate variability quantification.

BACKGROUND

Heart Rate Variability (HRV) quantifies the fluctuations of the lengths of consecutive heart beat intervals. HRV reflects the regularity of heart beats, with higher regularity implying lower HRV, and is a reliable descriptor of many physiological factors modulating the normal rhythm of the heart. HRV is a crucial diagnostic tool and provides a powerful means of observing the interplay between the sympathetic and parasympathetic nervous systems and is thought to reflect the heart's ability to adapt to changing circumstances by detecting and quickly responding to unpredictable stimuli. As such, HRV metrics are useful in characterizing physiological stress.

Presently, Holter monitors or other portable devices for are used to continuously monitoring various electrical activity of the cardiovascular system for at least 24 hours (often for two weeks at a time). Recent studies have indicated that the duration of time that a patient is monitored may improve the accuracy of the results.

For example, one recent study illustrated the need for long-term monitoring in detecting of recurrences after ablation for atrial fibrillation ("AF"). See N. Dagres, et. al., "Influence of the duration of holter monitoring on the detection of arrhythmia recurrences after catheter ablation of atrial fibrillation: Implications for patient follow-up," *International Journal of Cardiology*, vol. 139, no. 3, pp. 305-306, 2010. As is described in Dagres, a 24-hour Holter detected 59% of patients with those recurrences, a 48-hour Holter detected 67%, a 72-hour Holter detected 80%, and a 4-day recording detected 91% of the recurrences that were detected with a complete 7-day recording. Consequently, the study concluded that a Holter duration of less than 4 days misses a great portion of recurrences.

As the need to monitor patients for longer periods of times has developed, there has been a corresponding need for monitoring devices which are smaller, more power efficient, available on a variety of mobile platforms and with new lower RF protocols. This has led to the development of wearable ECG monitoring devices that are capable of continuously recording and transmitting ECG signals for 7-14 days or longer periods of time. In addition to the improved ability to track and transmit these signals, however, there is a need for improvements in analyzing the data so as to accurately and efficiently measure HRV.

The subject matter claimed herein is not limited to embodiments that solve any disadvantages or that operate only in environments such as those described above. Rather, this background is only provided to illustrate one exemplary technology area where some embodiments described herein may be practiced.

SUMMARY

According to an aspect of an embodiment, a computer readable storage medium is configured to cause a system to perform operations of computing the standard deviation of a plurality of K−1 most recent heart beat intervals and a current heart beat interval (I1) from a plurality of consecutive heart beat intervals, from a sum (S1) of K most recent heart beat intervals squared and the sum (S2) of the K most recent heart beat intervals and a Kth oldest heart beat interval (I2). The computer readable storage medium calculates an updated sum (S1') of S1 minus I2 squared plus I1 squared and the updated sum (S2') of S2 minus I2 plus I1, and a square root of the sum of the ratio of S1' to K and of the ratio of the square of S2' to the square of K.

The object and advantages of the embodiments will be realized and achieved at least by the elements, features, and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DESCRIPTION OF EMBODIMENTS

Figure 1:
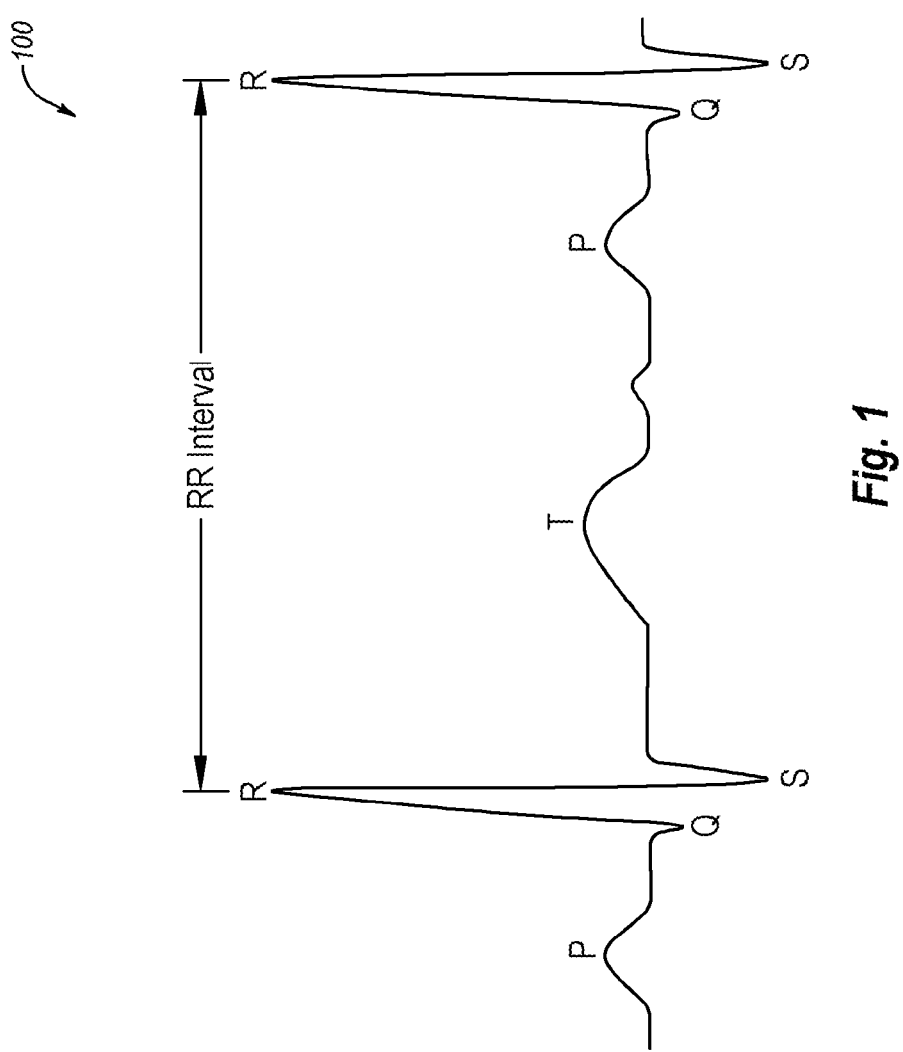
FIG. 1 is a graph including an example trace representing a normal heart rhythm.

Every person has an active sympathetic nervous system (SNS), which is responsible for inducing stress, and an active parasympathetic nervous system (PSNS), which is responsible for inducing relaxation. When a person is not stressed, the SNS and PSNS are in a healthy balance, which may be referred to as a baseline or non-stressed state.

One method of determining stress includes a cardiac sensor, such as a heart rate sensor, and a computing device such as a smartphone, a tablet computer, or a laptop computer which monitors HRV, as HRV is a measure of the balance between sympathetic mediators of heart rate (HR) (i.e. the effect of epinephrine and norepinephrine, released from sympathetic nerve fibres, acting on the sino-atrial and atrio-ventricular nodes), which increase the rate of cardiac contraction and facilitate conduction at the atrio-ventricular node, and parasympathetic mediators of HR (i.e. the influence of acetylcholine, released by the parasympathetic nerve fibres, acting on the sino-atrial and atrio-ventricular nodes), leading to a decrease in the HR and a slowing of conduction at the atrio-ventricular node. The cardiac sensor may be configured to generate a data signal corresponding to a measured heartbeat of a subject over time. The data signal generated by the cardiac sensor may include electrocardiography (ECG or EKG) data, for example.

HRV is the temporal variation between time intervals between consecutive heartbeats. On a standard electrocardiogram (ECG), for example, the maximum upwards deflection of a normal QRS complex is at the peak of an R wave, and the duration between two adjacent R wave peaks called an R-R interval. Typically, before HRV analysis is performed, a process is performed so as to remove of all non-sinus-node-originating beats. The resulting period between adjacent QRS complexes resulting from sinus node depolarizations is termed the N-N (normal-normal) interval, where HRV is the measurement of the variability of the N-N intervals.

In 1996, the European Society of Cardiology and the North American Society of Pacing and Electrophysiology formed a Task Force with the goal of standardizing measurement, physiological interpretation and clinical uses of HRV methods. Their accepted methods typically input a sequence of these N-N intervals and fall into the following categories:

Time Domain:
   (1) Simple metrics: including the mean NN interval, mean heart rate, difference between the longest and shortest NN interval, difference between day and night heart rates;
   (2) Statistical metrics (applied on longer periods of time, traditionally 24 hours): standard deviation of the NN intervals (SDNN) and its variations, the square root of the mean squared differences of successive NN intervals (RMSSD), the proportion of interval differences of successive NN intervals greater than 50 ms (pNN50); and
   (3) Geometrical interpretation metrics.
Frequency Domain: the standardized methods quantify the power within specific frequency bands via power spectral density analysis, where the primary metric is LF/HF, which is the ratio of the power within bands LF ([0.04 Hz, 0.15 Hz]) and HF([0.15 Hz, 0.4 Hz]).

Although these metrics have been standardized, they are typically calculated inefficiently using existing methods, resulting in high computational loads, requiring more processing time and decreased battery life.

For example, calculating pNN50, one of the simpler HRV metrics using existing algorithms for a sequence of k+1 NN intervals $(x_0, \ldots, x_k)$, the standard algorithm computes the percentage of successive NN interval differences whose absolute value is larger than 50 ms, or $$pNN50 = \frac{1}{k}\sum_{j=1}^{k} X_j, \text{ where } X_j \text{ is } 1 \text{ if } |x_j - x_{j-1}| > 50$$

and 0 otherwise.

Generally, when a new NN interval is received by the computing or processing device for interval $x_{k+1}$, pNN50' is computed for the sequence including NN intervals $(x_0, \ldots, x_{k+1})$, by recomputing the sum on the new sequence.

As is described more fully below, rather than inefficiently recomputing the metric, an embodiment described herein is designed to efficiently update at real-time various time domain and non-parametric frequency domain HRV metrics, including the central moment of the heart rate signal. By more efficiently updating these metrics, the systems and methods described herein provide real-time feedback long-term ambulatory recordings leading to decreased power consumption and allows for computation of metrics which were not previously possible at real-time speeds.

Embodiments of the present invention will be explained with reference to the accompanying drawings.

FIG. 1 is a graph including an example trace 100 representing a normal heart rhythm, arranged in accordance with at least some embodiments described herein. A cardiac sensor such as an ECG device may be configured to generate a data signal represented by such a trace by detecting electrical signals generated by the sinoatrial (SA) node of the heart, which electrical signals control the heart's rhythm.

The trace 100 includes various waves or portions labeled P, Q, R, S and T, some of which are sometimes grouped together and described as a complex, such as the QRS complex. In a normal heart rhythm, the SA node generates an electrical impulse which travels through the right and left atria. The P wave represents the electricity flowing through the atria. The QRS complex represents the flow through the ventricles as they contract to push the blood out from the heart. The T wave represents repolarization or the electrical resetting of the heart for the next beat. The next heart beat cycle begins at the next P wave.

As shown in FIG. 1, the RR interval is the time between successive R waves. Each RR interval corresponds to a heartbeat. Moreover, heart rate in terms of beats per minute is inversely proportional to the RR interval and may be calculated from the RR interval. Insofar as the length of each RR interval may vary from one heartbeat to the next, an instantaneous heart rate may be calculated for a single RR interval or an average heart rate may be calculated across multiple consecutive RR intervals. The variability of the RR interval from one heartbeat to the next is referred to as heart rate variability (HRV).

Figure 2A:
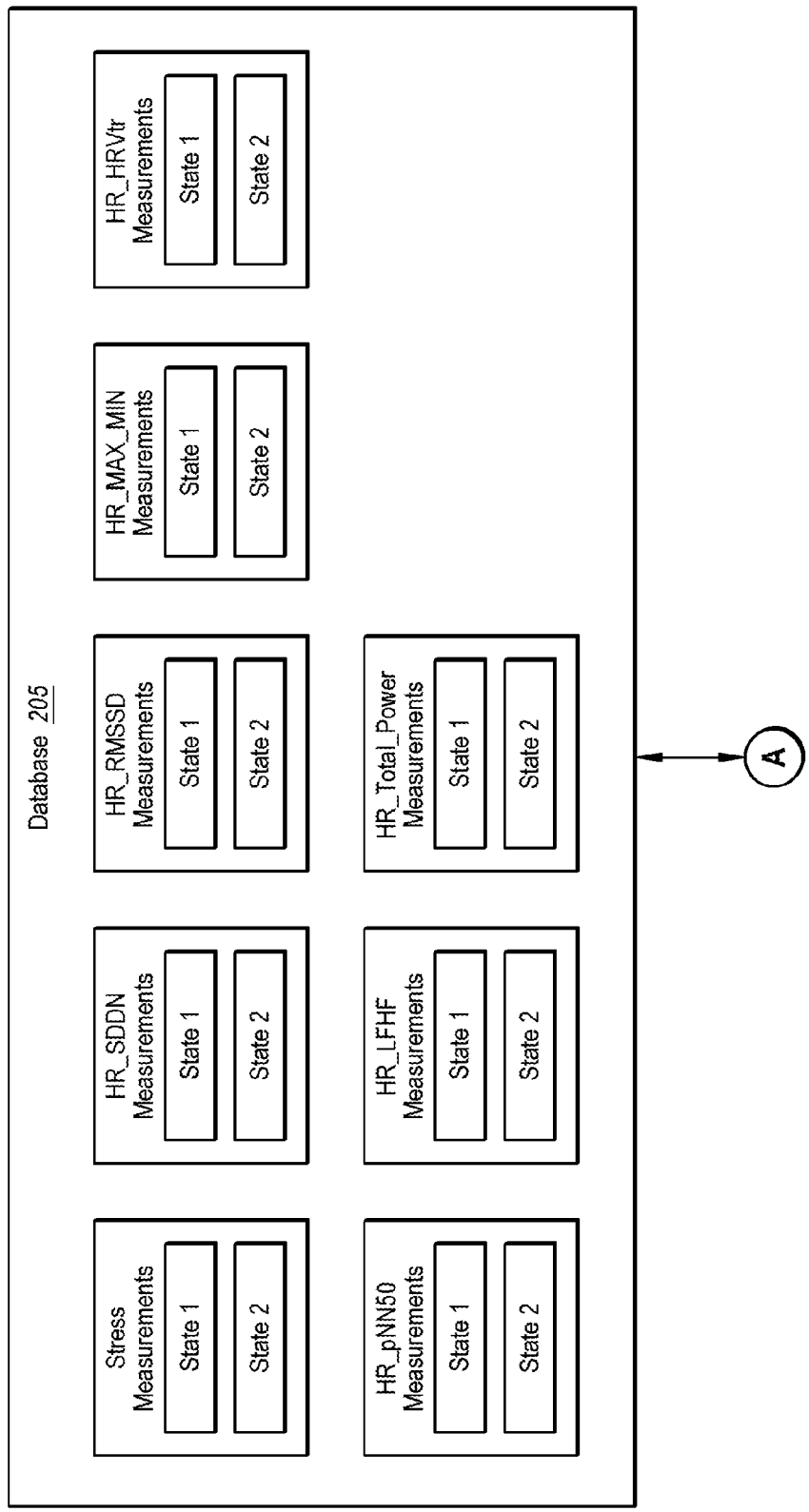
FIGS. 2A and 2B are block diagrams of an example system of determining stress based on RRIA.
Figure 2B:
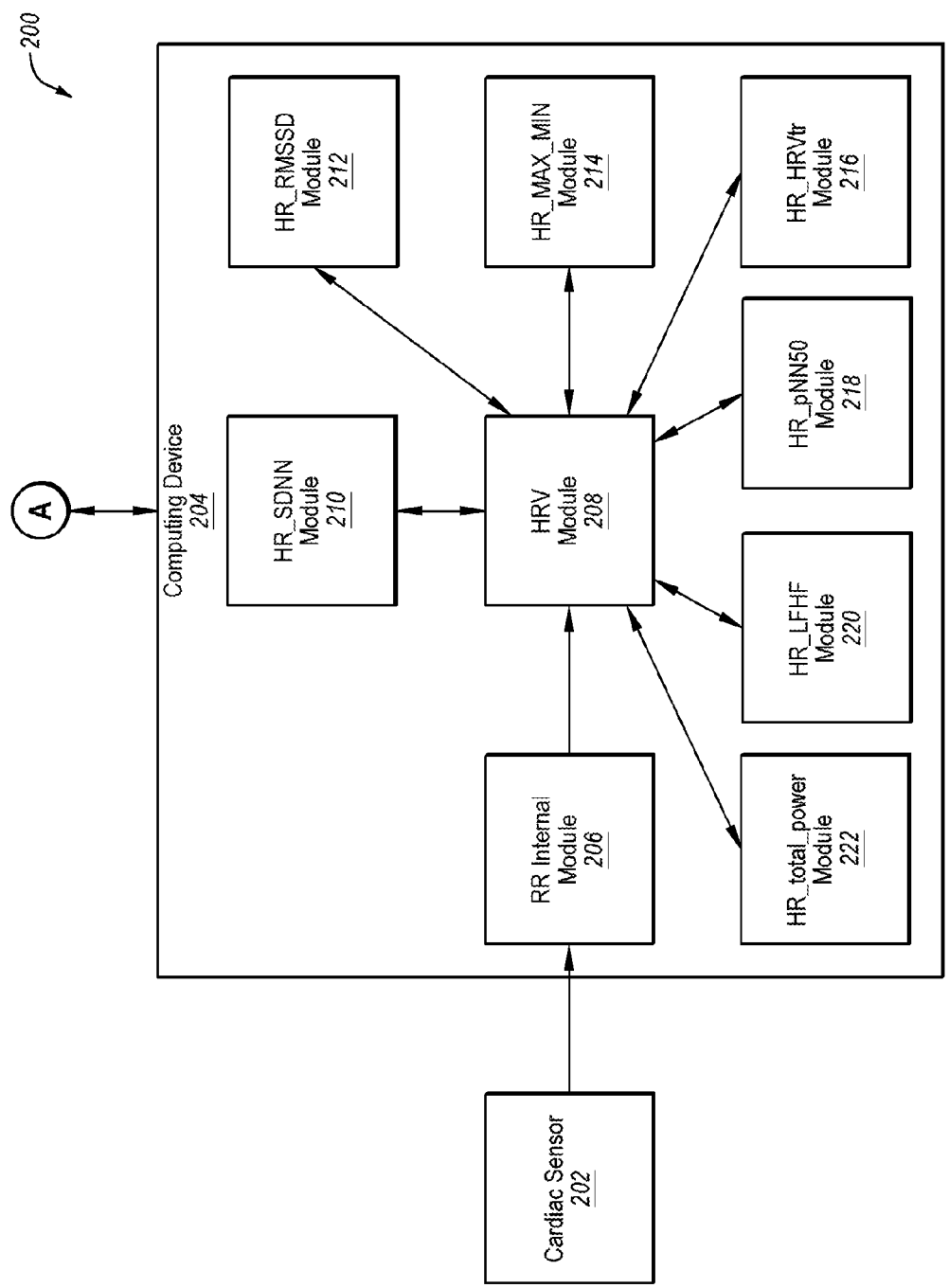

FIG. 2 is a block diagram of an example system 200 of determining stress based on a calculated central moment for HRV, arranged in accordance with at least some embodiments described herein. The system 200 may include a cardiac sensor 202 and a computing device 204. In some embodiments, the system 200 may further include a database 205. Although not shown, the system 200 may optionally further include one or more batteries and/or other mobile power supplies configured to power the computing device 204 and/or the cardiac sensor 202. In these and other embodiments, the system 200 may be implemented as a mobile system. Accordingly, the computing device 204 may include, but is not limited to, a smartphone, a tablet computer, a laptop computer, or other mobile computing device, as well as traditionally non-mobile computing devices such as desktop computers.

With continued reference to FIG. 2, the cardiac sensor 204 may be configured to generate a data signal including multiple consecutive RR intervals of a subject. The data signal generated by the cardiac sensor 204 may be visually represented by an ECG trace, such as the trace 100 of FIG. 1, for example. The cardiac sensor 204 may include, but is not limited to, an ECG (or EKG) device, a pulse oximeter, a Holter monitor, a photoplethysmograph (PPG), a finger-attached, chest-strap, or ear-clip type heart rate monitor, or other suitable cardiac sensor.

The computing device 204 may be communicatively coupled to the cardiac sensor 202 via a wired or wireless connection. The computing device 204 may be configured to receive the data signal generated by the cardiac sensor 202. The computing device 204 may additionally be configured to determine stress based on HRV. In some embodiments, for example, the computing device 204 may be configured to calculate HRV metrics for the subject from the data signal including the central moment of the HRV signal and may be further configured to calculate a subject's stress level from the HRV metric, by calculating a metric indicating the stress level of the subject based on the HRV metric.

Accordingly, the computing device 204 may include an RR interval module 206 and an HRV module 208. In order to calculate the HRV metric(s), the computing device 204 may additionally include a SDNN module 210 for calculating the SDNN of the heart rate signal, an RMSSD module 212 for calculating the RMSSD of the signal, a Max/Min module 214 for calculating the maximum and minimum heart rate of the signal, a HRVtr module 216 for calculating the triangular index of the signal, a pNN50 module 218 for calculating the pNN50 of the signal, a LFHF module 220 for calculating the LFHF of the signal, and/or a power spectral density module 222 for calculating the total power P of the signal. The RR interval module 206, the HRV module 208, the SDNN module 210, RMSSD module 212, Max/Min module 214, HRVtr module 216, pNN50 module 218, LFHF module 220, and/or total power module 222 may be implemented in software, hardware, or a combination thereof. When implemented at least partially in software, the computing device 204 may additionally include a memory and a processing device configured to execute computer instructions stored in the memory to cause the computing device 204, and more particularly the processing device, to perform the operations described with respect to the various modules 206, 208, 210, 212, 214, 216, 218, 220 and/or 222.

In general, the RR interval module 206 may be configured to receive the data signal generated by the cardiac sensor 202, the data signal including the multiple consecutive RR intervals. The RR interval module 206 may be further configured to calculate a length of time of each of the consecutive RR intervals from the data signal. Each RR interval may represent or correspond to a heartbeat.

The HRV module 208 may be configured to receive a sequence of NN intervals between adjacent QRS complexes resulting from sinus node depolarizations from the RR interval module 206. The HRV module 208 may be further configured to communicate with the various modules 210-222 to obtain various HRV data for the subject from the various modules 210-222.

As is described more fully below, each of the modules 210-222 may be configured to provide streaming updates by updating the various HRV metrics over sliding windows of time. For example, the HRV module 208 may calculate and continually update (1) SDNN or the root of the second central moment of a window of NN intervals, (2) RMSSD or the root of the second raw moment of a window of NN interval differences, (3) Maximum and Minimum RR intervals, (4) HRVtr of a window of NN intervals, (5) the pNN50 of the NN intervals, (6) the LF/HF or low-to-high frequency ratio of NN intervals, and (7) the total power of NN intervals. As is described more fully below, the HRV module 208 may be used to efficiently calculate a variety of HRV data by continuously updating data as new data is received in the HRV module 208.

As is described more fully below, the HRV module 208 and the modules 210-222 described herein use updating algorithms which utilize calculated and stored values from a previous window of NN intervals in order to efficiently compute the various HRV metrics each time a new data point is received, enabling the HRV module 208 and the modules 210-222 to reduce the computing time necessary to continuously generate HRV metrics.

Figure 3:
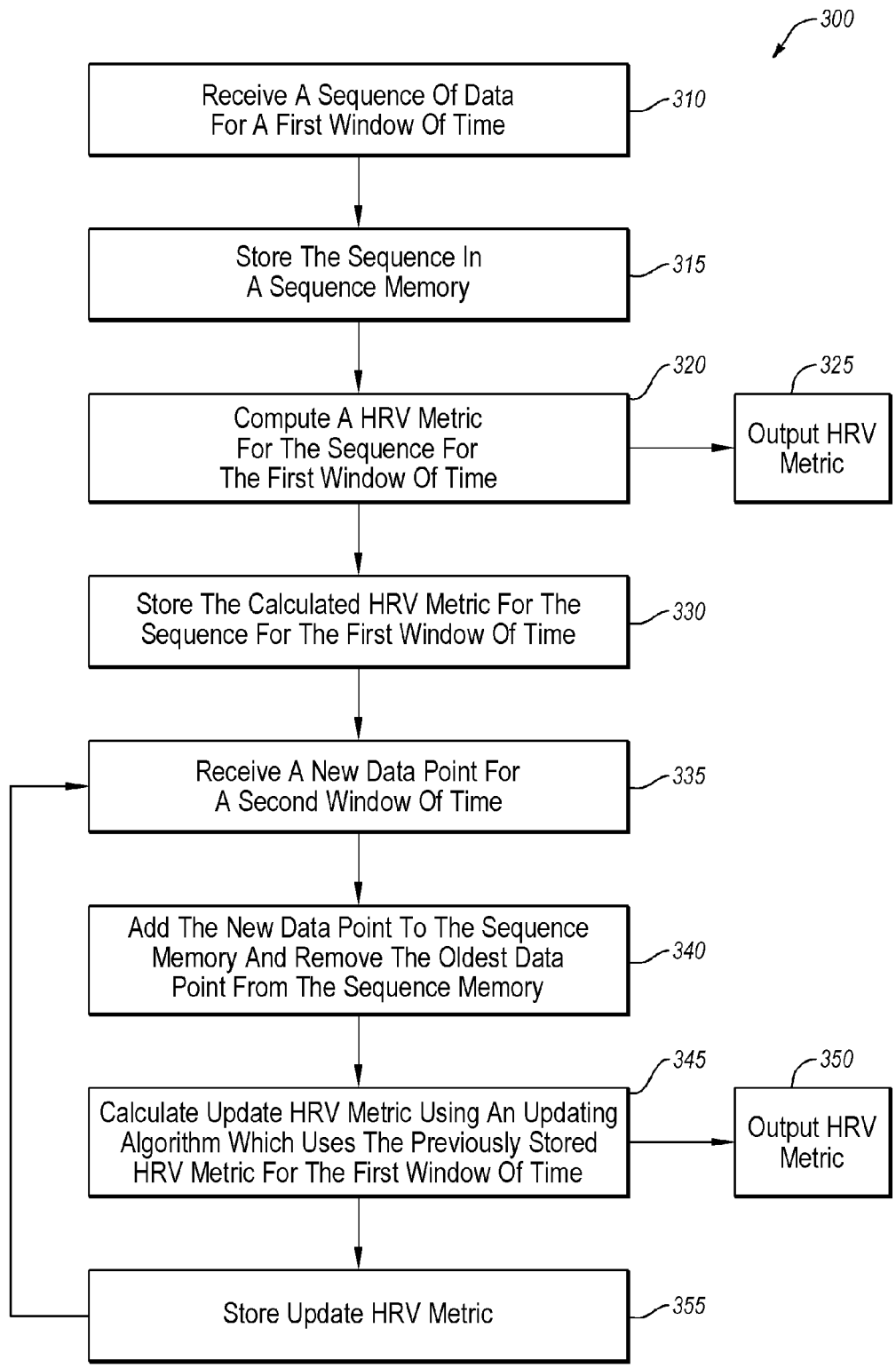
FIG. 3 is a block diagram of an example system of performing a streaming update of an HRV metric.

FIG. 3 is a block diagram of an example method 300 of performing a streaming update of an HRV metric, arranged in accordance with at least some embodiments described herein. The method 300 and/or variations thereof may be implemented, in whole or in part, by a system, such as the system 200 of FIG. 2. Alternately or additionally, the method 300 and/or variations thereof may be implemented, in whole or in part, by a processor or other processing device. Although illustrated as discrete blocks, various blocks may be divided into additional blocks, combined into fewer blocks, or eliminated, depending on the desired implementation.

Although FIG. 3 illustrates the system for performing streaming updates of a HRV metric generally, specific examples of algorithms which may be used to update specific HRV metrics are described more fully below. Further, the method may be performed by the HRV module 208 or any of the specific HRV metric modules 210-222.

The method 300 begins at block 310 as a sequence of data is received for a series of N-N intervals in a first window of time. Then, at block 320, the sequence is stored in a sequence memory. At block 330, a HRV metric is computed for the sequence for the first window of time and outputted at block 325 from the computing device 204 to the database 205, where the metric may be stored and eventually displayed. As is also described more fully below, the computed HRV metric may also be used by the HRV module 208 to evaluate a patient's stress level.

The HRV metric may also be stored at block 330 within the HRV module 208 to be used in subsequent calculations as is described more fully below. At 335 as a new data point is received from the RR Interval module 206 and sent to the HRV module 208, the new data point is added to the sequence memory and the oldest data point, now outside the streaming time window, is removed or deleted from the sequence memory. Using an updating algorithm which uses the previously stored HRV metric for the first window of time and the new data point such as those described more fully below, an updated HRV metric is calculated at block 345 and outputted at block 350. The new updated HRB metric is then stored block 355. When a new data point is received, the method 300 returns to block 335 and the method continues to calculate updated HRV metric for subsequent streaming time windows as subsequent data points are received.

I. Time Domain Methods

A. Computing Raw and Central Moments Over Sliding Windows

Figure 4:
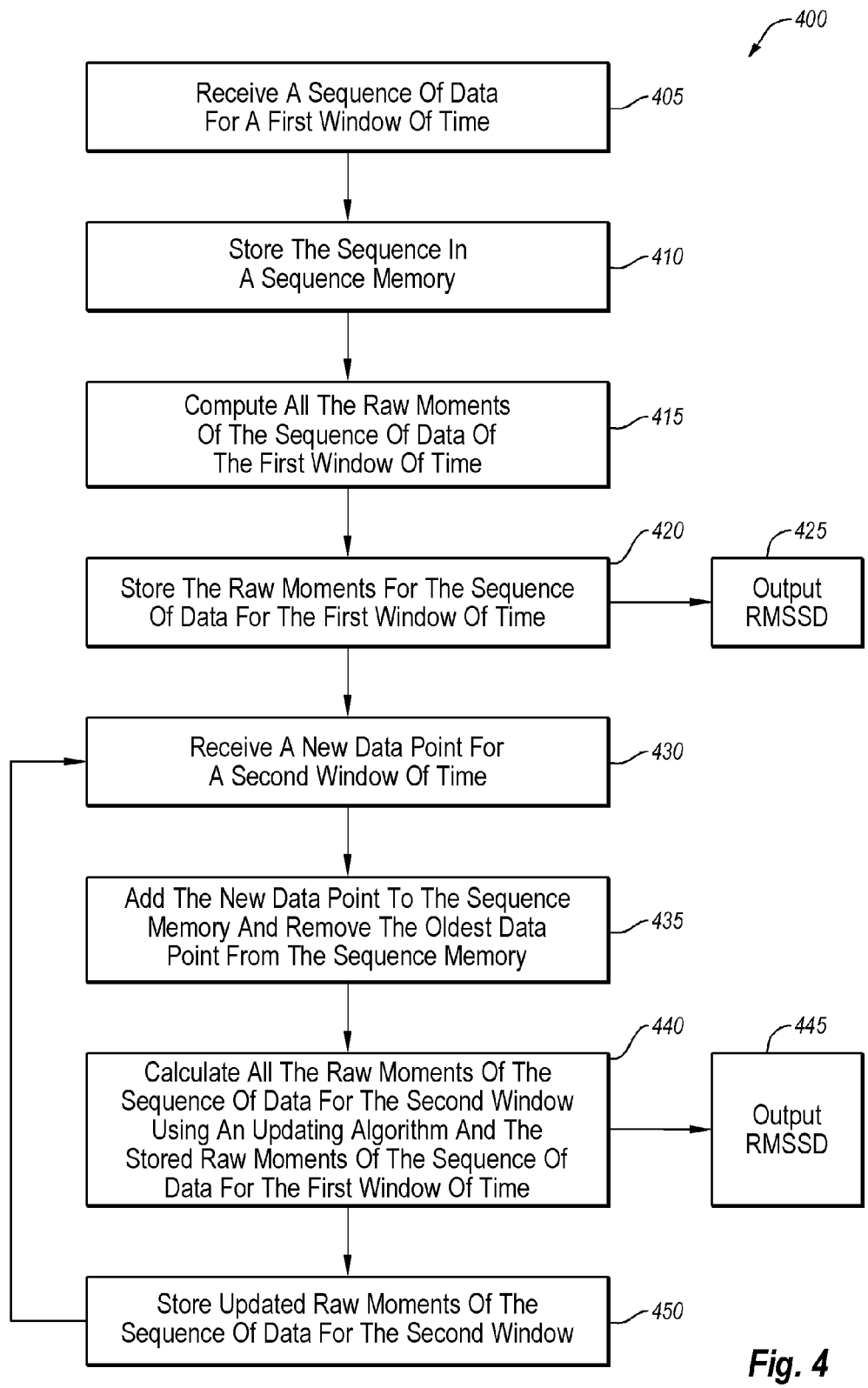
FIG. 4 is a block diagram of an example system of performing a streaming update of a raw moment over sliding windows to obtain the Root Mean Square of the Successive Differences (RMSSD) as a specific type of an HRV metric.
Figure 5:
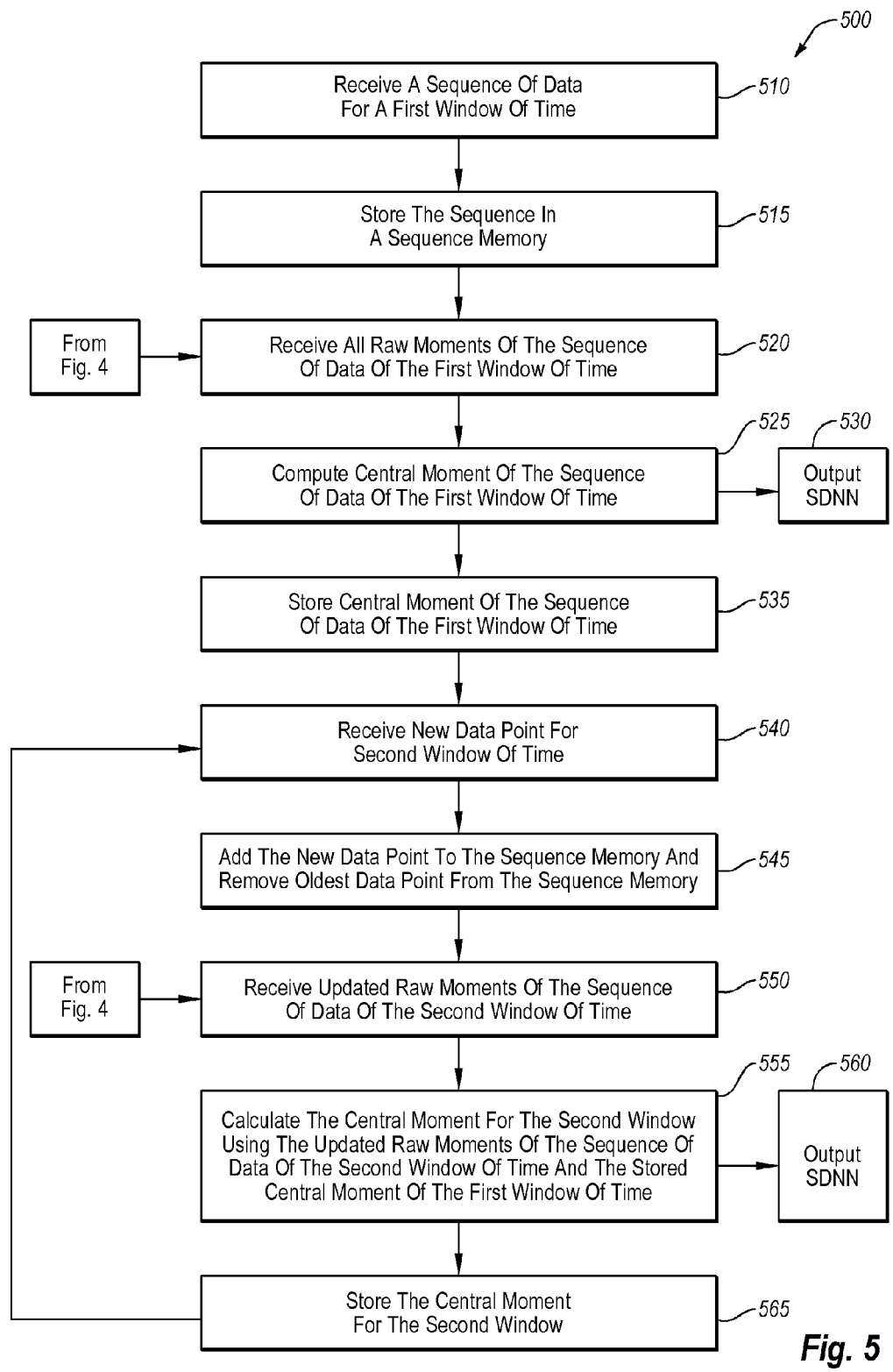
FIG. 5 is a block diagram of an example system of performing a streaming update of a central moment over sliding windows to obtain the standard deviation of NN intervals (SDNN) as another type of HRV metric.

FIG. 4 is a block diagram of an example method 400 of performing a streaming update of the raw moments of a sequence of N-N intervals over sliding windows of time, arranged in accordance with at least some embodiments described herein and FIG. 5 is a block diagram of an example method 500 of performing a streaming update of the central moments of a sequence of N-N intervals over sliding windows of time, arranged in accordance with at least some embodiments described herein, wherein the method 500 utilizes the raw moments calculated according to the method 400 illustrated in FIG. 4.

The methods 400, 500 and/or variations thereof may be implemented, in whole or in part, by a system, such as the system 200 of FIG. 2. Alternately or additionally, the methods 400, 500 and/or variations thereof may be implemented, in whole or in part, by a processor or other processing device. Although illustrated as discrete blocks, various blocks may be divided into additional blocks, combined into fewer blocks, or eliminated, depending on the desired implementation.

SDNN and RMSD are considered important HRV metrics. SDNN is the standard deviation or the second central moment of a sequence of N-N intervals, and RMSD is the root-mean-square successive difference, is a calculation of the square root of the mean of the squared differences between successive N-N intervals, or the second raw moment of a sequence of $\delta NN^2$ intervals, where $\delta NN(i) = |NN_i - NN_{i-1}|$. Hence, by calculating the second raw moment of a second using the method 400 of FIG. 4, RMSD may be outputted for a sliding window of time and using the method 500 of FIG. 5, SDNN may be outputted for the sliding window of time.

The method 400 for performing a streaming update of the raw moments of the sequence of N-N intervals and calculating RMSD begins at block 405 as a sequence of data is received for a series of N-N intervals in a first window of time. At block 410, the sequence is stored in a sequence memory. At block 415, the raw moments of the sequence of intervals for the first window of time are computed and outputted at block 425 from the computing device 204 to the database 205, where the RMSSD may be stored and eventually displayed.

The calculated RMSSD may also be stored at block 420 within the HRV module 208 or RMSSD module 212 to be used in subsequent calculations as is described more fully below. At block 430 as a new data point is received from the RR Interval module 206 and sent to the RMSSD module 212, the new data point is added to the sequence memory at block 435 and the oldest data point, now outside the streaming time window, is removed or deleted from the sequence memory. Using an updating algorithm which uses the previously stored RMSSD for the first window of time and the new data point such as those described more fully below, an updated RMSSD is calculated at block 440 and outputted at block 445. The new updated RMSSD is then stored block 450. When a new data point is received, the method 400 returns to block 430 and the method continues to calculate an updated RMSSD for subsequent streaming time windows as subsequent data points are received.

The method 500 for performing a streaming update of the central moments of the sequence of N-N intervals and calculating RMSD begins at block 510 as a sequence of data is received for a series of N-N intervals in a first window of time. At block 515, the sequence is stored in a sequence memory. At block 520, the raw moments of the sequence of intervals for the first window of time are received from the RMSSD module 212 as calculated in method 400, and the central moments of the sequence of data of the first window of time are calculated at block 525 and outputted as SDNN at block 530 from the computing device 204 to the database 205, where the SDNN may be stored and eventually displayed.

The calculated central moments may also be stored at block 535 within the HRV module 208 or SDNN module 210 to be used in subsequent calculations as is described more fully below. As a new data point is received at block 540 from the RR Interval module 206 and sent to the SDNN module 210, the new data point is added at block 545 to the sequence memory and the oldest data point, now outside the streaming time window, is removed or deleted from the sequence memory. The updated raw moments of the sequence of data of the second window of time are received at block 550 according to the method 400 described in FIG. 4. Using an updating algorithm which uses the previously stored central moments for the first window of time, the updated raw moments from block 550, and the new data point, updated central moments are calculated at block 555 and outputted at as an updated SDNN at block 560. The new updated central moments are then stored at block 565. When a new data point is received, the method 500 returns to block 540 and the method continues to calculated an updated central moments and output SDNN values for subsequent streaming time windows as subsequent data points are received.

The updating algorithm for calculating the RMSSD and SDNN is described below. As may be understood by one of skill in the art, the kth raw moment for a window of elements, or a predetermined sliding number of NN intervals $(x_1, \ldots, x_N)$ is defined as:

$$\mu'_k = \frac{1}{N} \sum_{n=1}^{N} x_n^k$$

where the mean $\mu = \mu'_1$.

The kth central moment is defined as:

$$\mu_k = \frac{1}{N} \sum_{n=1}^{N} (x_n - \mu)^k.$$

Rather than recalculating the kth central moment each time a new interval is received, the SDNN module 210 updates the kth central moment in O(k). Raw moments of any degree maybe updated in constant time. For $j = 1 \ldots k$, the unscaled sums:

$$\text{sum}_j = \sum_{n=0}^{N-1} x_n^j,$$

In one embodiment, the SDNN module 210 may use a ring buffer to store the N most recent data points. Upon receiving a new element $x_N$ at block 540, the SDNN module 210 extracts the oldest element $x_0$ from the buffer and add the new element $x_N$ into the ring buffer. The SDNN module 210 adds $x_N^j - x_0^j$ to $\text{sum}_j$ for $j = 1 \ldots k$. Consequently, the updated $\mu'_j$ is $sum_j/N$. Because the original elements remain stored in the ring buffer, those elements are reused for updating the raw moments of any degree.

Via binomial transform, the $k^{th}$ central moment may also be expressed as:

$$\mu_k = \sum_{n=0}^{k} (-1)^{k-n} \binom{k}{n} \mu'_n \mu^{k-n}.$$

Because each raw moment is updated in O(1) according to the method 400, all raw moments up to degree k maybe updated in O(k). Therefore, $\mu_k$ may also be updated in O(k) time. In one embodiment, only a single ring buffer containing the elements of the relevant window is used to maintain and calculate both the raw moments up to degree k and the central moment.

An example of an algorithm for updating the kth raw moment is included below:

| Algorithm 1 update_kth_moment(pt) |
| --- |
| Require: ring_buffer<integer> C(w) |
| Require: integer sum[1...k] |
| Require: integer coeff[0...k]  /* coeff[i] = $(-1)^{k-i}\binom{k}{i}$ */ |
| 1:    if C.full( ) then |
| 2:        last_pt = pop = C.pop_front( ) |
| 3:        for loop ∈ [1..k] do |
| 4:            sum[loop] −= last_pt |
| 5:            last_pt = last_pt · pop |
| 6:        end for |
| 7:    end if |
| 8:    new_pt = pt |
| 9:    for loop ∈ [1..k] do |
| 10:       sum[loop] += last_pt |
| 11:       new_pt = new_pt · pt |
| 12:    end for |
| 13:    C.push_back(pt) |
| 14:    moment = 0 |
| 15:    factor = 1 |
| 16:    for loop ∈ [1..k] do |
| 17:       moment += coeff[loop] · factor · sum[loop] |
| 18:       factor = factor · sum[1] / w |
| 19:    end for |
| 20:    moment = (moment + coeff[0] · factor) / w |

Using the algorithm listed above, the raw moments and central moments of sliding windows maybe continually calculated by updating their values in real time. Consequently, SDNN and RMSSD values maybe continually calculated and outputted in real time more efficiently than currently known in the art. Furthermore, in addition to calculating the central moments for a sliding window, the HRV module 208 may calculate a variety of other HRV metrics including those described below.

B. Computing Medians Over Sliding Windows

In an embodiment, the HRV module 208 may compute the median so as to update the median over a sliding window in O(1) expected time. Comparative evaluations have shown that the median of a sliding window of δNN intervals is one of the most valuable HRV algorithms and yields very intuitive connections with other HRV algorithms. For example, it is equal to that value X for which $\delta NN_X = 50\%$. It is also the value that separates the integral of the histogram of the elements in the sliding window into two equal parts.

1) Initialization Phase:

The initialization phase of one algorithm which may be implemented by the HRV module 208 is depicted on Algorithm 2 below. The first point is inserted into the ring buffer which contains the sliding window and clear the table that holds the histogram (where MaxValue is typically 100) and also mark the existence of the first data point into it. The first point is initially also the median. In this example, two auxiliary variables "balance" and "splitter" are also initialized to be utilized as is described more fully below.

| Algorithm 2 init median(w, first pt) |
| --- |
| Require: ring_buffer<integer> C(w) |
| Require: integer histogram[0..MaxValue] |
| Require: integer balance |
| Require: integer splitter |
| 1:    C.push_back(pt) |
| 2:    ∀entry ∈ [0...MaxValue] : histogram[entry] = 0 |
| 3:    histogram(first_pt) = 1 |
| 4:    balance = splitter = 0 |
| 5:    median = first_pt |

2) Update Phase:

The update portion of the median computation algorithm in the example described herein maintains three invariants. When positive, the first variable, balance denotes the number of sample points smaller than the current median that would have to be inserted into the histogram such that the current median value remains valid. Similarly, if negative, it denotes the number of sample points larger than the current median value that would have to be inserted such that the current median remains valid. Hence, in the algorithm below, balance∈[0,1].

The second variable, splitter is a bookkeeping variable. It denotes the exact position within all histogram[median] elements where the median would lie. More specifically, splitter elements would lie to the left while histogram [median]−splitter−1 elements would lie to the right. The actual median value is positioned at exactly position splitter within the elements of the median-th entry of the histogram. Through the balance invariant, the splitter invariant is maintained and through that, the median invariant is maintained. Hence, in the algorithm below, 0≤splitter≤histogram[median].

| Algorithm 3 update median(pt) |
| --- |
| 1:    if C.full( ) then |
| 2:       pop = C.front( ) |
| 3:       histogram[pop] − − |
| 4:       if pop < median then |
| 5:          balance ++ |
| 6:       else |
| 7:          balance − − |
| 8:       end if |
| 9:    end if |
| 10:    C.push back(pt) |
| 11:    histogram[pt] ++ |
| 12:    if pt < median then |
| 13:       balance − − |
| 14:    else |
| 15:       balance ++ |
| 16:    end if |
| 17:    if balance > 1 then |
| 18:       balance −= 2 |
| 19:       if ++splitter == histogram[median] then |
| 20:          splitter = 0 |
| 21:          repeat |
| 22:             median++ |
| 23:             until histogram[median] > 0 |
| 24:       end if |
| 25:    else if balance < 0 then |
| 26:       balance += 2 |
| 27:       if − −splitter < 0 then |

-continued

| Algorithm 3 update median(pt) |
|---|
| 28:                     repeat |
| 29:                         median-- |
| 30:                     until histogram[median] > 0 |
| 31:                     splitter = histogram[median] − 1 |
| 32:               end if |
| 33:               else if splitter = = histogram[median] then |
| 34:                   splitter = 0 |
| 35:                   repeat |
| 36:                       median++ |
| 37:                     until histogram[median] > 0 |
| 38:               end if |

In the Algorithm 3 shown above, lines 1-9 handle the steady-state case where the ring buffer is full. Before entering the new point, the earliest point that was entered is removed. Depending on its location in relation to the current median, the median value may have been invalidated. Consequently, the variable balance is updated to denote the number and relative position of new elements that would have to be entered into the histogram in order to keep the median valid.

Lines 10-16 add the new point to the ring buffer and the histogram, also properly updating the variable balance. At this point it is possible to determine if the median value requires updating. At the entry point, the variable balance may either be 0 or 1. After lines 1-16 have been executed, the balance variable may either be increased or decreased by at most 2, causing its new possible range to fall between [−2, 3]. The variable balance maybe modified to bring it back to the range dictated by the invariant.

If balance∈[2, 3], the only way to reduce the variable balance is to increase the median. Increasing the median position by 1 allows us to reduce balance by 2. This scenario is handled by the segment of Algorithm 3 shown in lines 17-24. The median value is moved to the right by increasing the variable splitter. If splitter becomes large enough such that it lies outside the histogram[median] limits, then it is reset and median is updated to the next non-empty histogram entry to its right. In a similar fashion, if balance∈[−2, −1], the only way to increase it is by decreasing the median. This symmetric case is handled by the segment of Algorithm 3 recited in lines 25-32.

The final segment of Algorithm 3, corrects a problem which may arise when the element that was originally popped or removed from the ring buffer was exactly at median, thus possibly invalidating the splitter invariant. This case is handled by segment 33-38.

Using the algorithm described above, it is possible for the HRV module 208 to continuously calculate the median over a sliding window as new data points are received by simply updating the median of the histogram rather than recalculating the median anew each time the new data points are received.

C. Computing Minimums/Maximums Over Sliding Windows

In an embodiment, the HRV module 208 may use a Max_Min module 214 may also compute the minimum and maximum values of a sequence of intervals in a particular sliding window. Algorithm 4 illustrates an exemplary embodiment of an algorithm which may be executed by the HRV module 208 and/or Max_Min module 214 to compute the maximum value of a sequence. A similar algorithm described briefly below maybe used to compute the minimum value of a sequence.

Returning to Algorithm 4, for every new element $x_t$, the $\max(x_{t-w+1}; \ldots, x_t)$ value is updated over a sliding window of w elements. The Max/Min module 214 may use a ring buffer C of length w. For each incoming element $x_t$, all elements that are smaller than or equal to $x_t$ are removed from the end of the ring buffer C. Then, $x_t$ is inserted into the ring buffer C. The maximum value of the sliding window is the first element of ring buffer C. The stored elements of the ring buffer C are time-stamped when added to the ring buffer C and are removed after w updates. Each element is added to and deleted from the ring buffer C exactly once, therefore updates maybe performed in amortized O(1) time.

| Algorithm 4 update_max(pt) |
|---|
| Require: ring_buffer< {element, timestamp} > C(w) |
| Require: integer counter |
| 1:     while (!C.empty( ) && C.back( ).element ≤ pt) do |
| 2:         C.pop_back( ) |
| 3:     end while |
| 4:     C.push_back( { element = pt, timestamp = ++counter } ) |
| 5:     if (C.front( ).timestamp == counter − w) then |
| 6:         C.pop_front( ) |
| 7:     end if |
| 8:     max = C.front( ).element |

While the specific algorithm for calculating a minimum value of a sliding window is not expressly included, the algorithm for computing the minimum is a slight modification of Algorithm 4 (where the inequality on Line 1 is reversed.) Using two separate ring buffers, it is possible to update the maximum and minimum values of a sliding window. Empirical observations have shown that the number of elements in these buffers does not grow significantly in size compared to w. In fact, it may be seen that they maintain a monotonically decreasing subsequence of the complete sliding window whose length is bounded by the difference between the maximum and the minimum element in the window. This is a small difference compared to w.

D. Computing Triangular Indices Over Sliding Windows

In another embodiment, the HRV module 208 may use a HRVtr module 216 may compute triangular indices over a sliding window. To compute the HRV triangular index (HRVtr), the density distribution of all N-N intervals is maintained in the sliding window. The density bin width is typically 7:8125 ms which corresponds to a sampling frequency of 128 Hz which is the standard ECG sampling rate per standardized protocol. HRVtr is defined as the ratio of the total N-N intervals over the frequency of the modal bin.

The total number of N-N intervals within a sliding window is readily available. In the algorithm depicted in Algorithm 5, HRVtr module 216 maintains a ring buffer C which contains the bin numbers for each element in the sliding window. Tuples {freq, bin} are maintained in a max-heap H, ordered on the bin frequencies. There exists a tuple in H for each bin, whose frequency is initially 0. In this example, a direct map is also maintained using a direct_map variable between the bin numbers and the corresponding tuple positions within H. When the HRVtr module 216 receives a new data point pt, the oldest element is removed from C, and its location is obtained in H via direct_map, the frequency of the corresponding tuple in H is reduced by 1and its location in H is adjusted via a heapify-down operation. Then, the bin number of pt is added into C and its position is detected via direct map in H. Then the corresponding tuple's frequency is increased by 1 and its position is readjusted in H via a heapify-up operation. Traditional heap operations heapify-down and heapify-up are extended such that whenever two tuples in H swap positions, their corresponding locations in direct_map are also appropriately updated.

---
Algorithm 5 update_triangular_index(pt)
---
Require: ring_buffer< integer > C(w)
Require: max_heap< {freq, bin} > H
Require: integer direct_map[BinCount]
  1:    Bin = pt /BinWidth
  2:    if C.full( ) then
  3:        heapify_down(direct_map[C.pop_front( )])
  4:    end if
  5:    C.push_back(bin)
  6:    heapify_up(direct_map[bin])
  7:    triangular_index = C.size( ) / H.top( ).freq
---

The algorithm's complexity is largely based on the complexity of the heapifyup and heapify-down operations, which is O(log BinCount), where BinCount is the total number of bins in the distribution and is typically 256. Using this algorithm, the space requirements are O(w+BinCount), where w is the length of the sliding window. Consequently, the HRVtr module 216 is able to efficiently calculate and update the HRV triangular index.

E. Computing pNN50 Over Sliding Windows

In another embodiment, the HRV module 208 may use a pNN50 module 218 to compute pNN50 over a sliding window in O(1) time. As previously described, all δNN values are stored in a ring buffer of length w. As shown in Algorithm 6 below, a counter $cnt_{50}$ counts the number of |δNN| values that are larger than 50. When the pNN50 module 218 receives a new element $x_N$, the oldest element $x_0$ is extracted from the buffer. If $|x_0|>50$ then $cnt_{50}$ is decreased by 1. If $|x_0|>50$ then $cnt_{50}$ is increased by 1. The metric pNN50 may then be obtained from $cnt_{50}$=w. Because the pertinent information per new data point is binary, a ring buffer of Boolean variables is stored and maintained instead of the actual data points, thereby decreasing memory requirements for the algorithm and improving the computational efficiency of the system.

---
Algorithm 6 update_pNN50(pt)
---
Require: ring_buffer< boolean > C(w)
Require: integer count
     1:    if C.full( ) then
     2:        count -= C.front( )
     3:    end if
     4:    C.push_back(|pt|)
     5:    Count += C.back( )
     6:    pNN50 = count /w
---

III. Frequency Domain Methods

In another embodiment, the HRV module 208 may also perform various domain methods. Power spectral Density (PSD) analysis is useful for understanding how power is distributed as a function of frequency. Typically, PSD is either estimated via regression analysis or, more commonly, via FFT analysis, with both approaches providing comparable results. The HRV measures employed are (1) the total power P, (2) the power within the VLF/LF/HF frequency bands ([0, 0.04 Hz]/[0.04 Hz, 0.15 Hz]/[0.15 Hz, 0.4 Hz]), (3) the normalized power within the LF/HF bands ($LF_{norm}$=LF/(P-VLF), $HF_{norm}$=HF/(P-VLF)), and (4) the ratio LF/HF. Ratio LF/HF is typically the more widely used metric. Before applying FFT, the unevenly spaced peak detection signal needs to be resampled.

Typically, resampling rates are between 2 and 4 Hz. Recently, a study performed on the effects of beat replacement and resampling concluded that a resampling rate of 7 Hz is appropriate as it allows for the resolution of heart rates of up to 210 bpm. Described herein is a method for updating Fourier coefficients in constant time is provided. As is described below, each coefficient maybe updated independently of the other coefficients. This allows for the update of just the appropriate subset of coefficients corresponding to the desired frequency bands, as opposed to updating them individually at each iteration.

A. Updating FFT Coefficients Over Sliding Windows

The HRV module 208 may also compute FFT coefficients over a sliding window using a LFHF module 220. For a $\{x\}_t$ a streaming sequence of numbers a sliding window of a length L, Algorithm 7 illustrates a method which may be used by the LFHF module 220 for updating the Fourier coefficients of window $(x_{t-L+1}, \ldots, x_t)$ for every new element $x_t$ received at time t.

Let:

$$X_k^t = \sum_{n=0}^{L-1} x_{n+t-L+1} \cdot e^{-2\pi i k n/L}$$

be the Fourier coefficients for window $(x_{t-L+1}, \ldots, x_t)$. Then $$X_k^t = \sum_{n=1}^{L-1} x_{n+t-L} \cdot e^{-2\pi i k(n-1)/L} + x_t \cdot e^{-2\pi i (L-1)/L} =$$

$$\left( \sum_{n=1}^{L-1} x_{n+t-L} \cdot e^{-2\pi i k n/L} \right) \cdot e^{2\pi i k/L} + x_t \cdot e^{-2\pi i (L-1)/L} =$$

$$(X_k^{t-1} - x_{t-L} + x_t) \cdot e^{2\pi i k/L}$$

Each Fourier coefficient $X_k^t$ may be updated from $X_k^{t-1}$ in constant time. More specifically, if all powers of the L-th primitive root of unity $e^{2\pi i/L}$ are precomputed then one real addition and one complex multiplication may suffice for updating $X_k^t$. Alternatively, one additional complex multiplication per coefficient is sufficient for generating the appropriate root power. As such, the LFHF module 220 is able to efficiently calculate LFHF by updating the value over a series of streaming windows of time.

---
Algorithm 7 update_LFHF(pt)
---
Require: ring_buffer< integer > C(w)
Require: complex fft_coeff[w]
Require: complex unity_root[w]
    1:    old = 0
    2:    if C.full( ) then
    3:        old = C.front( )
    4:    end if
    5:    C.push_back(pt)
    6:    lf = hf = 0
    7:    for index ∈ [$VLF_{TH}$...$HF_{TH}$] do
    8:        fft_coeff[index].re += pt - old
    9:        $factor_1$ = fft_coeff[index].re · unity_root[index].re
  10:       $factor_2$ = fft_coeff[index].im · unity_root[index].im
  11:       $factor_3$ = (fft_coeff[index].re +fft_coeff[index].im) · (unity_root[index].re + unity_root[index].im)
  12:       fft_coeff[index].re = $factor_1$ - $factor_2$
  13:       fft_coeff[index].im = $factor_3$ - $factor_1$- $factor_2$
  14:       P = fft_coeff[index].$re^2$ + fft_coeff[index].$im^2$ -continued

| Algorithm 7 update_LFHF(pt) |
|---|
| 15:         if index < $LF_{TH}$ then |
| 16:             lf += P |
| 17:         else |
| 18:             hf += P |
| 19:         end if |
| 20:     end for |
| 21:     LFHF = lf/hf |

B. Computing Power Spectral Densities Over Sliding Windows

The HRV module 208 may also compute power spectral densities over a sliding window using the total power module 222 using an algorithm as described below. The periodogram of $\{x\}_t$ is defined as:

$$P(k) = \begin{cases} \frac{1}{N^2}|X_k|^2, & k = 0, N/2 \\ \frac{2}{N^2}|X_k|^2, & k = 1, \ldots, \frac{N}{2} - 1 \end{cases}$$

P(k) is an estimate of the power spectrum of the time series at frequency $$f_k = \frac{k}{\Delta N},$$

where $\Delta$ is the sampling period. Since $x_t$ is real, $X_k = \overline{X_{N-k}}$. By Parseval's theorem:

$$\sum_{k=0}^{N/2} P(k) = \frac{1}{N}\sum_{j=0}^{N-1}|x_j|^2$$

Algorithm 8 below illustrates an example of an algorithm which may be implemented by the HRV module 208 and total power module 222 to compute the power spectrum of the time series.

| Algorithm 8 update_total_power(pt) |
|---|
| Require: ring_buffer< integer > C(w) |
| Require: integer sum |
|    1:         if C.full( ) then |
|    2:             pop = C.front( ) |
|    3:             sum -= pop · pop |
|    4:         end if |
|    5:         C.push_back(pt) |
|    6:         sum += pt · pt |
|    7:         total_power = sum / w |

Using the algorithms and methods described above, embodiments described herein are capable of performing streaming updates of central moments for HRV quantification including providing streaming updates of SDNN and RMSSD values. More specifically, using the method and algorithms previously described SDNN, RMSSD, NN Median, NN Interval Range and pNN50 metrics are computed more efficiently from the data points on the sliding window without reusing previously computed information.

B. Results

Figure 8:
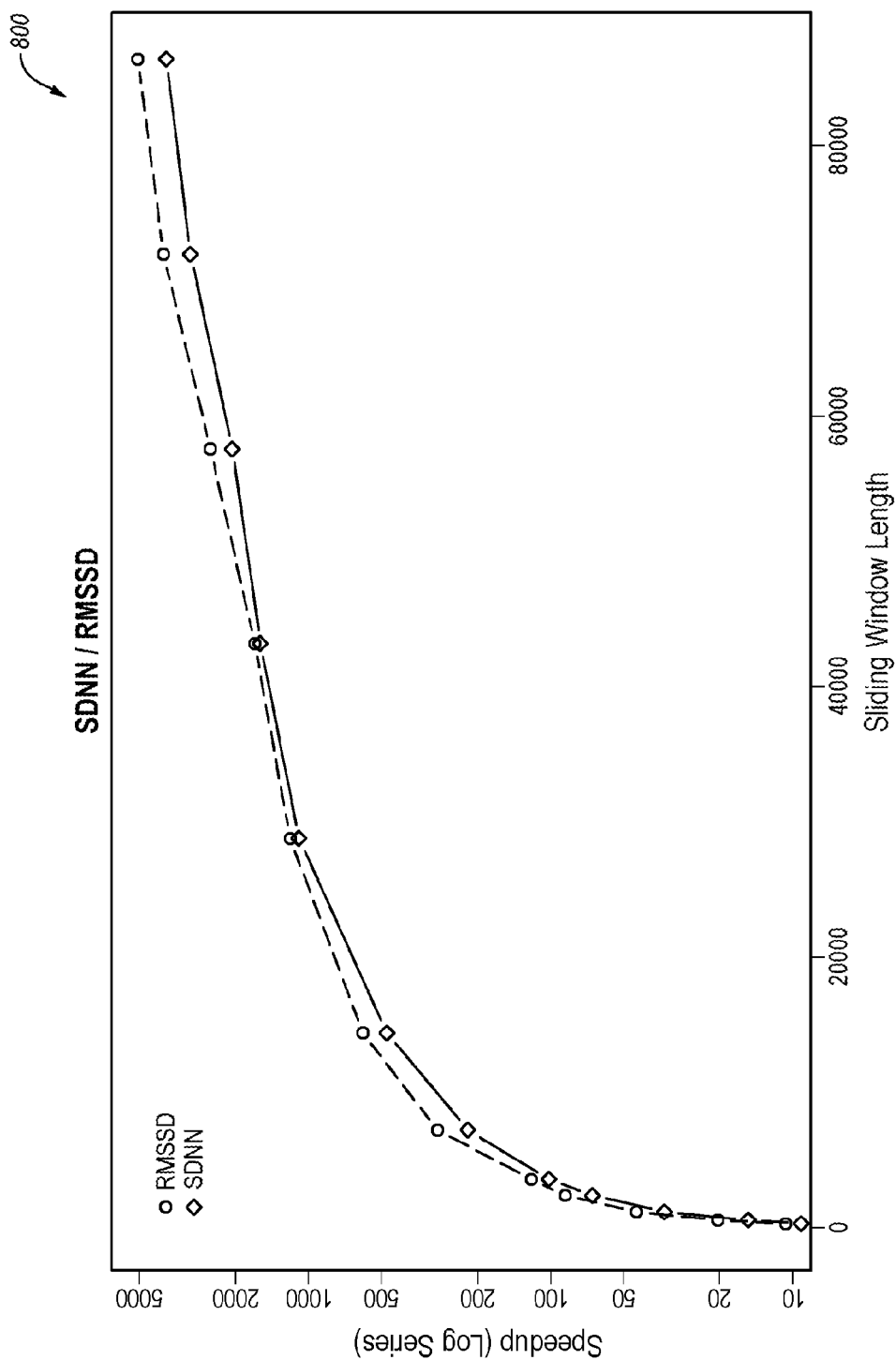
FIG. 8 is a graph illustrating the performance ratios between known implementations for obtaining SDNN and RMSSD as compared to one embodiment of the system and method for obtaining streaming updates of central moments for heart rate variability quantification described herein.

FIG. 8 is a graph 800 which presents the performance ratios between the proposed and classical implementations for SDNN and RMSSD. As shown therein, speedups that are linearly increasing with the window size. The methods and systems described herein demonstrated speedups of more than two orders of magnitude for typical use-case scenarios, which consequently translate to significantly longer battery lives for mobile systems that adopt them. For the most computationally heavy frequency domain methods, the algorithms described herein allow for real-time updates in cases where it was not previously possible.

As previously described, the HRV metrics calculated above, including the SDNN and RMSSD may be subsequently used to determine the stress of a patient. An example of a system and method capable of using SDNN and RMSDD values to perform stress evaluations is found in U.S. patent application Ser. No. 13/745,099, filed Jan. 18, 2013, entitled "STRESS MODEL BASED ON RR INTEGRAL AVERAGE," which is herein incorporated in its entirety.

Figure 6:
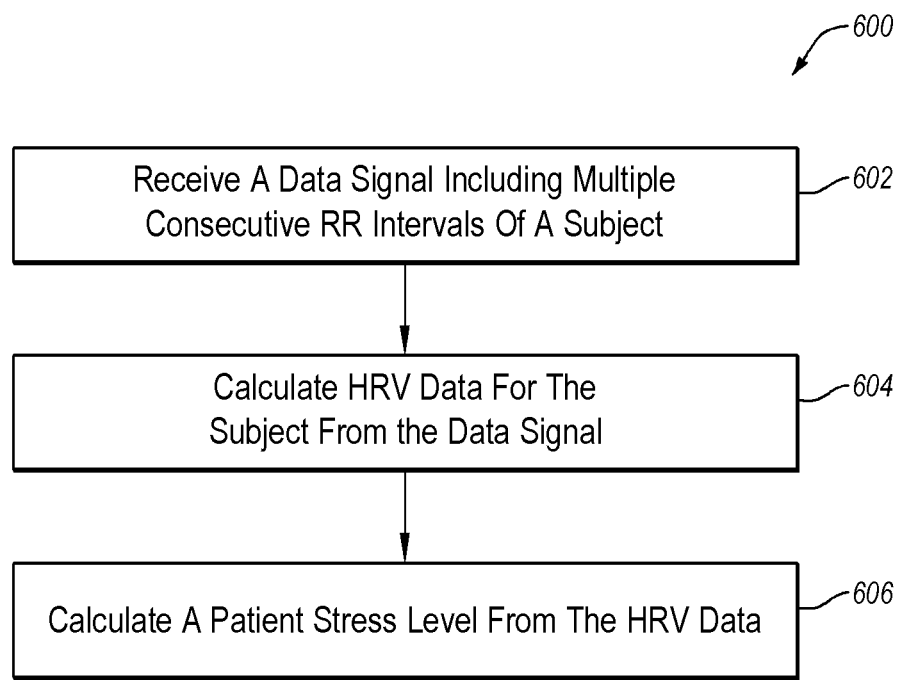
FIG. 6 shows an example flow diagram of a method of determining stress using the SDNN metric.

FIG. 6 shows an example flow diagram of a method 600 of determining stress based on HRV data, arranged in accordance with at least some embodiments described herein. The method 600 and/or variations thereof may be implemented, in whole or in part, by a system, such as the system 200 of FIG. 2. Alternately or additionally, the method 600 and/or variations thereof may be implemented, in whole or in part, by a processor or other processing device. Although illustrated as discrete blocks, various blocks may be divided into additional blocks, combined into fewer blocks, or eliminated, depending on the desired implementation.

The method 600 may begin at block 602 in which a data signal including multiple consecutive RR intervals of a subject is received. For example, such a data signal may be received by the computing device 204 from the cardiac sensor 202 of FIG. 2.

In block 604, HRV data for the subject may be calculated from the data signal. As is described above, the HRV data may include a variety of HRV data including the SDNN, RMSSN, mean, maximum/minimum values, HRVtr, pNN50, LFHF and the total power of the data signal. Furthermore, as is described above the HRV data may be continually updated over a series of streaming time windows.

In block 606, a stress value may calculated from the HRV data.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Alternately or additionally, the stress level or other HRV values may be determined at multiple different times. In this and other examples, the data signal may include a first data signal generated when the subject is in a first state, the HRV data may include first HRV data, representing a baseline stress level of the subject. Accordingly, the method 600 may further include assessing a current stress level of the subject by receiving a second data signal including multiple consecutive RR intervals of the subject at a current time. Second HRV data may be calculated for the subject from the second data signal as explained above. A second stress level may be calculated from the second HRV data. The two values may be compared to determine whether the subject is in a stressed state based on the comparison.

Determining whether the subject is in a stressed state based on the comparison may include determining that the subject is in a stressed state at the current time or the second HRV value, respectively, is less than the first HRV value, or determining that the subject is in a non-stressed state at the current time when the second HRV value, respectively, is greater than the first HRV value.

In some embodiments, the method 600 may further include recommending a stress-reduction treatment for the subject to reduce the current stress level in response to determining that the subject is in a stressed state at the current time. The stress reduction treatment may include medication, counseling, meditation, one or more mental or physical exercises, or postponement of an imminent medical procedure, or the like or any combination thereof.

Figure 7:
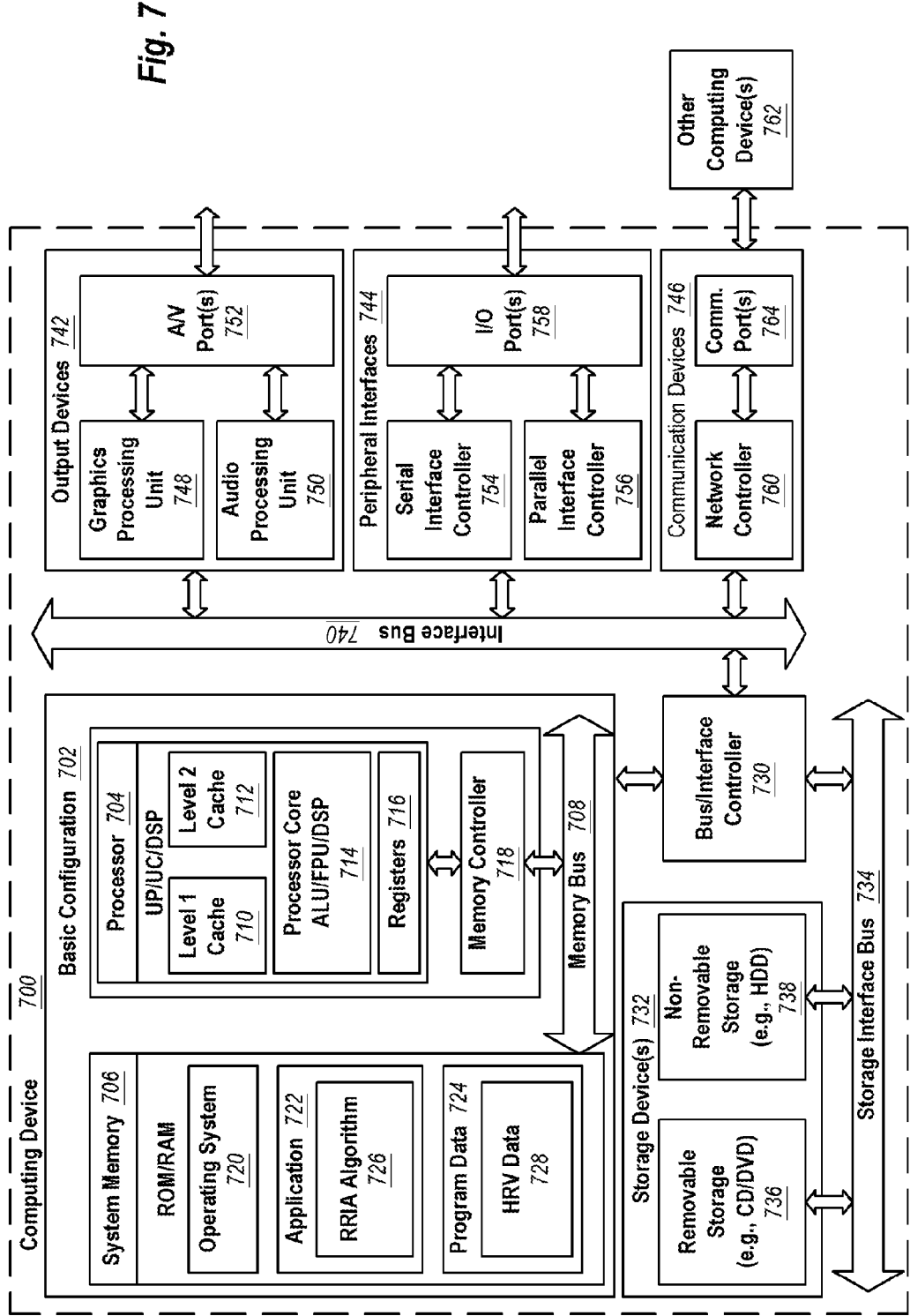
FIG. 7 is a block diagram illustrating an example computing device that is arranged for obtaining streaming updates of central moments for heart rate variability quantification and determining stress, all arranged in accordance with at least some embodiments described herein.

FIG. 7 is a block diagram illustrating an example computing device 700 that is arranged for performing streaming updates of central moments for HRV quantification, arranged in accordance with at least some embodiments described herein. The computing device 700 may correspond to the computing device 204 and/or may include or be connected to the database 205 of FIG. 2, for example. In a very basic configuration 702, the computing device 700 may include one or more processors 704 and a system memory 706. A memory bus 708 may be used for communicating between the processor 704 and the system memory 706.

Depending on the desired configuration, the processor 704 may be of any type including but not limited to a microprocessor (µP), a microcontroller (µC), a digital signal processor (DSP), or any combination thereof. The processor 704 may include one more levels of caching, such as a level one cache 710 and a level two cache 712, a processor core (or cores) 714, and registers 716. An example processor core 714 may include an arithmetic logic unit (ALU), a floating point unit (FPU), a digital signal processing core (DSP Core), or any combination thereof. An example memory controller 718 may also be used with the processor 704, or in some implementations the memory controller 718 may be an internal part of the processor 704. The processor 704 may be configured to perform one or more of the operations described herein by, for example, executing computer instructions or code loaded into the system memory 706 and/or by executing computer instructions or code line-by-line without using the system memory 706.

Depending on the desired configuration, the system memory 706 may be of any type including but not limited to volatile memory (such as Random Access Memory (RAM)), non-volatile memory (such as Read Only Memory (ROM), flash memory, etc.) or any combination thereof. The system memory 706 may include an operating system 720, one or more applications 722, and program data 724. The application 722 may include an RRIA algorithm 726 that is arranged to perform one or more of the operations associated with obtaining and processing a data signal including multiple consecutive RR intervals to determine stress of the subject as described herein, including one or more of the operations described with respect to FIG. 6A. Alternately or additionally, the application 722 may include an algorithm arranged to perform one or more of the operations described with respect to FIG. 6B. More generally, the application 722 may be executed by the processor 704 to cause the computing device 700 to perform the functions as described herein. The program data 724 may include HRV data 728 indicating the heart rate variability of the subject, which HRV data 728 may include an HRV histogram as is described herein. In some embodiments, the application 722 may be arranged to operate with the program data 724 on the operating system 720 such that stress of a subject may be determined based on the RRIA and/or according to other stress models.

The computing device 700 may have additional features or functionality, and additional interfaces to facilitate communications between the basic configuration 702 and other devices and interfaces. For example, a bus/interface controller 730 may be used to facilitate communications between the basic configuration 702 and one or more data storage devices 732 via a storage interface bus 734. The data storage devices 732 may be removable storage devices 736, non-removable storage devices 738, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer-readable instructions, data structures, program modules, or other data.

The system memory 706, the removable storage devices 736 and the non-removable storage devices 738 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by the computing device 700. Any such computer storage media may be part of the computing device 700.

The computing device 700 may also include an interface bus 740 for facilitating communication from various interface devices (e.g., output devices 742, peripheral interfaces 744, and/or communication devices 746) to the basic configuration 702 via the bus/interface controller 730. Example output devices 742 include a graphics processing unit 748 and an audio processing unit 750, which may be configured to communicate to various external devices such as a display or speakers via one or more A/V ports 752. Example peripheral interfaces 744 include a serial interface controller 754 or a parallel interface controller 756, which may be configured to communicate with external devices such as input devices (e.g., keyboard, mouse, pen, voice input device, touch input device, etc.) or other peripheral devices (e.g., printer, scanner, etc.) via one or more I/O ports 758. An example communication device 746 includes a network controller 760, which may be arranged to facilitate communications with one or more other computing devices 762 over a network communication link via one or more communication ports 764.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer-readable media as used herein may include both storage media and communication media.

The computing device 700 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. The computing device 700 may also be implemented as a personal computer including both laptop computer and non-laptop computer configurations.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it would be understood that the various changes, substitutions, and alterations could be made hereto without departing from the spirit and scope of the invention.

What is claimed is:

1. A computer readable storage medium having computer readable instructions stored thereon that are executable by a system to perform or control performance of operations comprising:
    receiving a data signal generated by a cardiac sensor that is configured to measure heart beats of a subject and generate the data signal that represents the measured heart beats;
    computing a standard deviation of a plurality of K−1 most recent heart beat intervals and a current heart beat interval (I1) from a plurality of consecutive heart beat intervals included in the data signal, from a sum (S1) of K most recent heart beat intervals squared and a sum (S2) of the K most recent heart beat intervals and a Kth oldest heart beat interval (I2); and
    calculating an updated sum (S1') of S1 minus I2 squared plus I1 squared and an updated sum (S2') of S2 minus I2 plus I1, and a square root of a sum of a ratio of S1' to K and of a ratio of a square of S2' to a square of K.

2. The computer readable storage medium of claim 1 being further configured to calculate a stress level of a subject based on the calculated updated sum S1'.

3. The computer readable storage medium of claim 1 being further configured to calculate an additional heart rate variability metric of the K−1 most recent heart beat intervals, the additional heart rate variability metric being selected from the group consisting of a maximum heart rate, a minimum heart rate, a triangular index, a proportion of heart beat interval differences of successive heart beat intervals greater than 50 milliseconds, a low-to-high frequency ratio, and a total power.

4. The computer readable storage medium of claim 1, wherein the updated sum S1' is recalculated each time a new heart beat interval is received at the computer readable storage medium to provide streaming updates of the sum S1' for a plurality of consecutive heart beat intervals of a window of time.

5. A system for performing heart rate variability quantification, the system comprising:
    a cardiac sensor configured to measure heart beats of a subject and generate a data signal based on the heart beats intervals of the subject;
    a computing device communicatively coupled to the cardiac sensor, the computing device configured to:
        compute a standard deviation of a plurality of K−1 most recent heart beat intervals and a current heart beat interval (I1) from a plurality of consecutive heart beat intervals included in the data signal, from a sum (S1) of K most recent heart beat intervals squared and a sum (S2) of the K most recent heart beat intervals and a Kth oldest heart beat interval (I2); and
        calculate an updated sum (S1') of S1 minus I2 squared plus I1 squared and an updated sum (S2') of S2 minus I2 plus I1, and a square root of a sum of a ratio of S1' to K and of a ratio of a square of S2' to a square of K.

6. The system of claim 5, wherein the cardiac sensor comprises an electrocardiography device or a pulse oximeter.

7. The system of claim 5, wherein the computing device comprises a smartphone, a tablet computer, or a laptop computer.

8. The system of claim 5, the computing device being further configured to determine a stress level of a subject based on the updated sum SI' and the system being further configured to quantify physiological stress.

9. The system of claim 5, the computing device being further configured to calculate an additional heart rate variability metric of the K−1 most recent heart beat intervals, the additional heart rate variability metric being selected from the group consisting of a maximum heart rate, a minimum heart rate, a triangular index, a proportion of heart beat interval differences of successive heart beat intervals greater than 50 milliseconds, a low-to-high frequency ratio, and a total power.

10. The system of claim 5, wherein the updated sum S1' is recalculated each time a new heart beat interval is received by the computing device from the cardiac sensor to provide streaming updates of the sum S1' for a plurality of consecutive heart beat intervals of a window of time.

11. The system of claim 5, further comprising a database communicatively coupled to the computing device and having stored thereon the updated sum S1' and the updated sum S2'.

* * * * *